United States Patent [19]

Matson et al.

[11] Patent Number: 4,598,145

[45] Date of Patent: Jul. 1, 1986

[54] ALBACARCINS V AND M

[75] Inventors: James A. Matson, Fayetteville; Robert W. Myllymaki, Syracuse; Terrence W. Doyle; James A. Bush, both of Fayetteville, all of N.Y.

[73] Assignee: Bristol-Myers Company, New York, N.Y.

[21] Appl. No.: 600,232

[22] Filed: Apr. 16, 1984

Related U.S. Application Data

[62] Division of Ser. No. 408,307, Aug. 16, 1982, Pat. No. 4,461,831.

[51] Int. Cl.$^4$ .................. C07H 7/04; C12P 19/00
[52] U.S. Cl. ........................ 536/1.1; 536/16.8; 536/18.1; 435/119
[58] Field of Search ............... 536/1.1, 16.8, 18.1; 514/23

[56] References Cited

PUBLICATIONS

J. Antibiotics 34: 1544–1555 (1981) Balitz et al.
J. Antibiotics 34: 266–275 (1981) Nakano et al.
Agric. Biol. Chem. 44: 1157–1163 (1980) Hatano et al.
Can. J. Chem. 59: 3018–3020 (1981) Findlay et al.
Antibiotiki 22: 963–967 (1977) Gauze et al.
Antibiotiki 23: 675–676 (1978) Gauze et al.
Soviet Journ. of Bioorg. Chem. 4(8): 798–802 (1978) Kulyaeva et al.
Wei, et al., "The Jour. of Antibiotics", vol. XXXV, No. 4, Apr., 1982, pp. 545–548.
Wei, et al., "Chem. Abst.", vol. 97, 1982, p. 16702(u).
Weiss et al., "Chem. Abst.", vol. 98, 1983, p. 232(a).

Primary Examiner—Johnnie R. Brown
Attorney, Agent, or Firm—David M. Morse

[57] ABSTRACT

Novel antitumor antibiotics designated herein as albacarcins M and V are produced by fermentation of *Streptomyces albaduncas* strain C-38291 (ATCC 39151). The new antibiotics possess antibacterial activity and also inhibit the growth of mammalian tumors such as P388 leukemia in mice.

2 Claims, No Drawings

ALBACARCINS V AND M

This is a division application of our co-pending application Ser. No. 408,307 filed Aug. 16, 1982, now U.S. Pat. No. 4,461,831.

BACKGROUND OF THE INVENTION

1. Field of the Invention

The present invention relates to two novel polycyclic antitumor antibiotic compounds designated herein as albacarcin M and albacarcin V and to their preparation by fermentation of a new strain of *Streptomyces albaduncus* designated herein as *Streptomyces albaduncus* strain C38291 (ATCC 39151).

2. Description of the Prior Art

Isolation of the polycyclic antitumor agents named gilvocarcins V, M and E from the fermentation broth of *Streptomyces anandii* subsp. *araffinosus* strain C-22437 (ATCC 31431) is disclosed in *J. Antibiotics* 34: 1544–1555 (1981). The gilvocarcin antibiotics have the structures shown below:

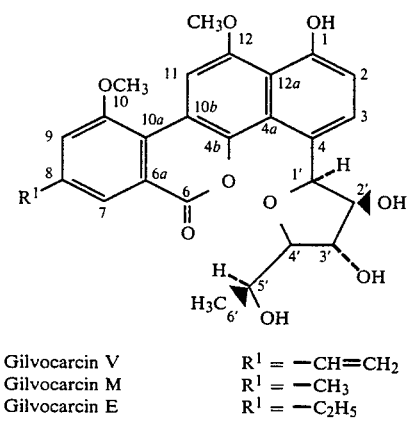

| | |
|---|---|
| Gilvocarcin V | $R^1 = -CH=CH_2$ |
| Gilvocarcin M | $R^1 = -CH_3$ |
| Gilvocarcin E | $R^1 = -C_2H_5$ |

As noted in the above-mentioned *J. Antibiotics* reference, gilvocarcins V and M were previously reported in *J. Antibiotics* 34: 266–275 (1981) as being isolated from the fermentation broth of *Streptomyces gilvotanareus* (NRRL 11382).

Gilvocarcin V and gilvocarcin M are the same as toromycin A and toromycin B, respectively, disclosed in *Agric. Biol. Chem.* 44: 1157–1163 (1980).

The antitumor antibiotic designated as ravidomycin Ia is disclosed in *Can. J. Chem.* 59: 3018–3020 (1981). Ravidomycin Ia, isolated from the fermentation broth of *Streptomyces ravidus*, has the structure

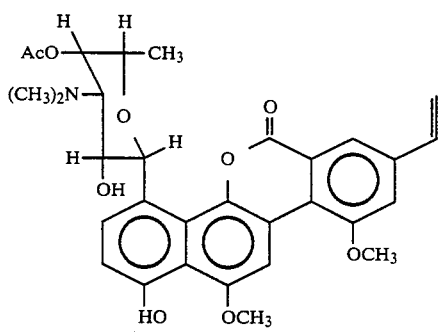

Ravidomycin Ia thus possesses the same aglycone moiety as gilvocarcin V (toromycin A).

The antitumor antibiotic designated as virenomycin is disclosed in *Antibiotiki* 22: 963–967 (1977); see also *Antibiotiki* 23: 675–676 (1978), *Soviet Journal of Bioorganic Chemistry* 4(8): 798–802 (1978) and *Encyclopedia of Antibiotics*, Second Edition, J. S. Glasby, Ed., pg. 457, Wiley-Interscience, Chichester-New York-Brisbane-Toronto, 1979. Virenomycin is isolated from the fermentation broth of *Streptomyces virens* strains 3831 and 3931/183. While the sugar moiety has been identified (see *Soviet Journal of Bioorganic Chem.* reference above), the structure of the remaining portion has never been reported. Virenomycin, which has the same sugar moiety as the antibiotics of the present invention, is reported to have a "comparatively low antitumor activity and narrow spectrum" (*Antibiotiki* 22: 963–967 at 967, 1977).

SUMMARY OF THE INVENTION

The present invention provides the polycyclic antitumor antibiotics albacarcin M and albacarcin V and a process for their preparation and isolation in a purified state substantially free of co-produced substances. The new antibiotics are obtained by cultivating an albacarcin M- and/or albacarcin V-producing strain of *Streptomyces albaduncus* having the identifying characteristics of strain C38291 (ATCC 39151) in an aqueous nutrient medium containing assimilable sources of carbon and nitrogen under submerged aerobic conditions until a substantial amount of albacarcin M and albacarcin V are produced by said organism in said culture medium and then recovering the albacarcin M and albacarcin V from said culture medium in substantially pure form.

The albacarcin M and albacarcin V antibiotics of the present invention have been found to exhibit antimicrobial activity and to inhibit the growth of tumors in experimental animals.

DETAILED DESCRIPTION

The albacarcin M and albacarcin V antibiotics provided by the present invention have been determined to have the structures

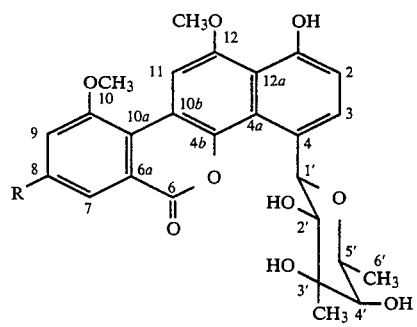

wherein R is $-CH_3$ (albacarcin M) or $-CH=CH_2$ (albacarcin V).

Compound albacarcin V is a yellow amorphous solid having a molecular formula of $C_{28}H_{28}O_9$ and a molecular weight of 508.555. It is composed of the elements carbon, hydrogen and oxygen.

Elemental analysis data is as follows: Calculated for $C_{28}H_{28}O_9 \cdot H_2O$: C, 63.87; H, 5.74; O(by difference), 30.39. Found: C, 63.54; H, 5.58; O(by difference), 30.88.

The infrared absorption spectrum of albacarcin V when pelleted in KBr exhibits characteristic bands at the following frequences expressed in reciprocal centimeters: 3400, 2980, 2940, 1705, 1625, 1610, 1590, 1510, 1490, 1450, 1435, 1370, 1335, 1330, 1250, 1190, 1160, 1150, 1130, 1065, 1010, 995, 975, 945, 915, 870, 850, 830, 780 and 720.

The ultraviolet absorption spectrum of albacarcin V was determined in methanol (0.02096 g/l). Observed absorption maxima and absorptivities were as follows: 392 nm ($\epsilon = 7272$), 286 nm ($\epsilon = 33,970$), 246 nm ($\epsilon = 33,259$).

Optical rotation values for albacarcin V are as follows:

$[\alpha]^{24°}_{Na(589)}$ (c=0.3, DMSO)= $-9.7°$.
$[\alpha]^{24°}_{Hg(578)}$ (c=0.3, DMSO)= $-10°$.
$[\alpha]^{24°}_{Hg(546)}$ (c=0.3 DMSO)= $-14°$.

A proton magnetic resonance spectrum of albacarcin V dissolved in DMSO was determined with a Bruker Model WM-360 Spectrometer operating at 360 MHz. Observed chemical shifts and pattern descriptions are as follows: δ9.82(s, 1H, ArOH), 8.48(s, 1H, H—11), 8.00(s, 1H, H—7), 7.85(d, J=8.22, 1H, H—3), 7.74(s, 1H, H—9), 6.98(d, J=8.22, 1H, H—2), 6.93(dd, J=15.82 and 10.76, 1H, —CH=CH$_2$), 6.14(d, J=15.82, 1H, —CH=CH—), 6.04(d, J=7.59, 1H, H=1'), 5.51(d, J=10.76, 1H, —CH=CH—), 4.60(d, J=6.32, 1H, OH), 4.52(m, 1H, H—5'), 4.17(s, 3H, OCH$_3$), 4.12(s, 3H, OCH$_3$), 3.69(t, J=9.43, H—4'), 3.16(d, J=6.29, H—3'), 1.21(s, 3H, 3'—CH$_3$), 1.03(d, J=6.29, 3H, 5'—CH$_3$).

A carbon-13 magnetic resonance spectrum of albacarcin V dissolved in DMSO was determined with a Bruker Model WM-360 Spectrometer operating at 90.5 MHz. Observed chemical shifts and assignments are as follows:

| No. | Chemical Shift (ppm) | Multiplicity | Assignment |
|---|---|---|---|
| 1 | 159.8 | s | 6 |
| 2 | 157.3 | s | 10 |
| 3 | 153.2 | s | 1 |
| 4 | 151.8 | s | 12 |
| 5 | 142.4 | s | 4b |
| 6 | 138.7 | s | 8 |
| 7 | 135.1 | d | 8a |
| 8 | 129.3 | d | 3 |
| 9 | 128.0 | s | 4 |
| 10 | 125.1 | s | 4a |
| 11 | 122.9 | s | 6a |
| 12 | 121.9 | s | 10a |
| 13 | 118.9 | d | 9 |
| 14 | 117.1 | t | 8b |
| 15 | 115.1 | s | 12a |
| 16 | 114.6 | d | 2 |
| 17 | 113.2 | s | 10b |
| 18 | 112.1 | d | 7 |
| 19 | 101.5 | d | 11 |
| 20 | 75.8 | d | 1' |
| 21 | 74.6 | d | 5' |
| 22 | 73.1 | s | 3' |
| 23 | 72.6 | d | 4' |
| 24 | 70.7 | d | 2' |
| 25 | 56.6 | q | OCH$_3$ |
| 26 | 56.2 | q | OCH$_3$ |
| 27 | 23.8 | q | 3'-CH$_3$ |
| 28 | 17.0 | q | 6' |

Compound albacarcin M is a yellow amorphous solid having a molecular formula of $C_{27}H_{28}O_9$ and a molecular weight of 496.484.

The infrared absorption spectrum of albacarcin M when pelleted in KBr exhibits characteristic bands at the following frequencies expressed in reciprocal centimeters: 3400, 2980, 2940, 1710, 1615, 1590, 1505, 1490, 1450, 1430, 1370, 1340, 1300, 1249, 1190, 1165, 1145, 1130, 1060, 1030, 1010, 990, 975, 955, 850, 820, 780, 715, 650, 615.

The ultraviolet absorption spectrum of albacarcin M was determined in methanol (0.01019 g/l). Observed absorption maxima and absorptivities were as follows: 382 nm ($\epsilon = 9731$), 305 nm ($\epsilon = 10,724$) 275 nm ($\epsilon = 31,825$), 266 nm ($\epsilon = 24,973$) and 244 nm ($\epsilon = 43,343$).

Optical rotation values for albacarcin M are as follows:

$[\alpha]^{24°}_{Na(589.3)}$ (c=0.03, DMSO)= $-14.9°$.
$[\alpha]^{24°}_{Hg(578)}$ (c=0.03, DMSO)= $-14.9°$.
$[\alpha]^{24°}_{Hg(546)}$ (c=0.3, DMSO)= $-22.3°$.

A proton magnetic resonance spectrum of albacarcin M dissolved in DMSO was determined with a Bruker Model WM-360 Spectrometer operating at 360 MHz. Observed chemical shifts and pattern descriptions are as follows: δ9.83(s, 1H, ArOH), 8.47(s, 1H, H—11), 7.84(d, J=9.49, 1H, H—3), 7.77(s, 1H, H—7), 7.49(s, 1H, H—9), 6.96(d, J=9.49, 1H, H—2), 6.04(d, J=9.49, 1H, H—1'), 4.59(d, J=7.91, 1H, H—5'), 4.53(m, 1H, OH), 4.20(s, 1H, OH), 4.18(d, J=9.49, 1H, OH), 4.11(s, 6H, OCH$_3$), 3.70(t, J=9.49, 1H, H—4'), 3.16(d, J=9.49, 1H, H—3'), 1.27(s, 3H, H—8a), 1.20(d, J=7.91, 3H, H—6').

A carbon-13 magnetic resonance spectrum of albacarcin M dissolved in DMSO was determined with a Bruker Model WM-360 Spectrometer operating at 90.5 MHz. Observed chemical shifts and assignments are as follows:

| No. | Chemical Shift (ppm) | Multiplicity | Assignment |
|---|---|---|---|
| 1 | 159.9 | s | 6 |
| 2 | 156.8 | s | 10 |
| 3 | 153.2 | s | 1 |
| 4 | 151.6 | s | 12 |
| 5 | 141.9 | s | 4b |
| 6 | 140.3 | s | 8 |
| 7 | 129.1 | d | 3 |
| 8 | 127.8 | s | 4 |
| 9 | 125.1 | s | 4a |
| 10 | 121.4 | s | 6a |
| 11 | 121.0 | d | 9 |
| 12 | 120.8 | s | 10a |
| 13 | 118.7 | d | 2 |
| 14 | 114.9 | s | 12a |
| 15 | 113.3 | s | 10b |
| 16 | 111.7 | d | 7 |
| 17 | 101.5 | d | 11 |
| 18 | 75.8 | d | 1' |
| 19 | 74.6 | d | 5' |
| 20 | 73.1 | s | 3' |
| 21 | 72.6 | d | 4' |
| 22 | 70.7 | d | 2' |
| 23 | 56.3 | q | 10-OCH$_3$ |
| 24 | 56.1 | q | 12-OCH$_3$ |
| 25 | 23.8 | q | 3'-CH$_3$ |
| 26 | 21.0 | q | 8-CH$_3$ |
| 27 | 17.0 | q | 6' |

The antibiotics of the present invention may be prepared according to the fermentation and isolation procedures described below.

The Producing Organism

The antibiotics of the present invention may be prepared by cultivating an albacarcin M and/or albacarcin V-producing strain of *Streptomyces albaduncus* in an aqueous nutrient medium under submerged aerobic conditions until a substantial amount of albacarcin M and/or albacarcin V is produced by said organism in said culture medium.

The preferred producing organism is a novel strain of *Streptomyces albaduncus* designated herein as *Streptomyces albaduncus* strain C38291. This strain was isolated from a soil sample collected in Columbia. A biologically pure culture of strain C38291 has been deposited with the American Type Culture Collection, Rockville, Md., and added to their permanent collection of microorganisms as ATCC 39151.

Characteristics of the above-mentioned preferred strain are described in detail below.

Strain C38291 (ATCC 39151)

Strain C38291 forms substrate and aerial mycelia (0.5$\mu$ in width). Both mycelia are long, well branched and not fragmented into short filaments. Spore chains are born monopodially on aerial mycelia or at hyphal tips. The spore chains form open or irregular short spirals and hooks, and contain 10–30 spores in a chain. The spores are spherical, oval or barrel-shaped (0.8 by 0.8–0.9$\mu$), and have a spiny surface. Sporangia, motile spores and sclerotia are not observed.

Strain C38291 grows well in all media including Czapek's agar. The aerial mycelium is poorly formed in most media such as Czapek's and ISP (International Streptomyces Project) agars, but forms abundantly on Bennett's agar. Gray aerial mycelium is formed in ISP medium Nos. 3 and 7, and Bennett's agar. Yellow or grayish olive green aerial mycelia are observed in Czapek's agar, ISP medium Nos. 2, 4 and 5, and glucose-asparagine agar. Therefore, the aerial mycelium of strain C38291 is similar to that of three color series, Yellow, Green and Gray. Yellow and green colors of the aerial mycelium of strain C38291 are likely to be derived from the diffused yellow or dark olive green pigments of the substrate mycelium. Thus, the intrinsic color of the aerial mycelium of strain C38291 is deduced to be gray. Strain C38291 produces reddish diffusible pigment in ISP medium Nos. 1, 2 and 7 and Bennett's agar, the color being red in alkali and yellow in acid. Melanoid pigment is not produced. The cultural characteristics are shown below in Table I.

TABLE I
Cultural Characteristics of Strain C38291

| | | |
|---|---|---|
| Tryptone-yeast extract broth (ISP No. 1) | G: | moderate; forms light olive brown pellets |
| | D: | yellowish pink (26) |
| Sucrose-nitrate agar (Czapek's agar) | G: | moderate |
| | R: | dark yellowish brown (78) |
| | A: | poor, light grayish olive (109) |
| | D: | deep yellowish brown (75) |
| Glucose-asparagine agar | G: | moderate |
| | R: | colorless to dark grayish yellow (91) |
| | A: | scant to poor, yellowish gray (93) to yellowish white (92) |
| | D: | none |
| Glycerol-asparagine agar | G: | moderate |
| | R: | dark yellowish brown (78) |
| | A: | poor, yellowish gray (93) to light gray (264) |
| | D: | none to deep yellowish brown (75) |
| Inorganic salts-starch agar (ISP No. 4) | G: | moderate |
| | R: | light olive brown (94) |
| | A: | moderate, light gray (264) |
| | D: | none to deep yellowish brown (75) |
| Tyrosine agar | G: | moderate |

TABLE I-continued
Cultural Characteristics of Strain C38291

| | | |
|---|---|---|
| (ISP No. 7) | R: | deep yellowish brown (75) to dark brown (59) |
| | A: | poor to moderate, yellowish gray (93) to light gray (264) |
| | D: | dark brown (59) |
| Nutrient agar | G: | poor |
| | R: | colorless |
| | A: | scant, yellowish white (92) |
| | D: | none |
| Yeast extract-malt extract agar (ISP No. 2) | G: | moderate |
| | R: | light yellowish brown (76) to dark olive (108) |
| | A: | poor to moderate, light olive gray (112) to medium gray (265) |
| | D: | deep reddish brown (41) |
| Oatmeal agar (ISP No. 3) | G: | poor |
| | R: | colorless to grayish yellow (90) |
| | A: | poor, light olive gray (112) to medium gray (265) |
| | D: | none to light olive brown (94) |
| Bennett's agar | G: | moderate |
| | R: | dark olive brown (96) to dark reddish brown (44) |
| | A: | moderate, grayish yellowish brown (80) |
| | D: | medium reddish brown (43) |
| Peptone-yeast extract-iron agar (ISP No. 6) | G: | poor |
| | R: | colorless |
| | A: | none |
| | D: | dark olive brown (96) |

*observed after incubation at 28° C. for 3 weeks
**Abbreviation: G = Growth; R = Reverse color; A = Aerial mycelium; D = Diffusible pigment
***Color and number in parenthesis follow the color standard in "Kelly, K. L. & D. B. Judd: ISCC-NBS color-name charts illustrated with Centroid Colors. U.S. Dept. of Comm. Cir. 553, Washington, D.C., Nov., 1975".

The growth of strain C38291 is inhibited by streptomycin or tetracycline, but not by benzylpenicillin, ampicillin or erythromycin. The sodium chloride tolerance is seen at 8% or less, but not at 10% or more. Melanin is not produced from L-3,4-dihydroxy phenylalanine (L-DOPA). Among eleven diagnostic sugars described in *Bergey's Manual*, 8th ed. (1974), only raffinose is not utilized by strain C38291. The physiological characteristics and utilization of carbohydrates are shown in Tables II and III, respectively.

TABLE II

| Physiological Characteristics of Strain C38291 | | |
|---|---|---|
| Test | Response | Method or medium used |
| Range of temperature for growth | Maximal growth at 37° C. to 43° C. Moderate growth at 28° C. and 45° C. No growth at 7° C. and 50° C. | Bennett's agar |
| Gelatin liquefaction | Liquefied | Glucose-peptone-gelatin medium |
| Starch hydrolysis | Hydrolyzed | Starch agar plate |
| Reactions in skimmed milk | Not coagulated and completely peptonized | Difco skimmed milk |
| Formation of melanoid pigment | Not produced | Tyrosine agar, peptone-yeast-iron agar and tryptone-yeast extract broth |
| Tyrosinase reaction | Negative | Arai's method* |
| Nitrate reduction | Negative | Czapek's sucrose-nitrate broth and glucose-yeast |

TABLE II-continued
Physiological Characteristics of Strain C38291

| Test | Response | Method or medium used |
|---|---|---|
| Acid tolerance | Growth at pH 4.5. No growth at pH 4.0 | extract broth Yeast extract-malt extract agar |
| NaCl tolerance | Growth at 8% or less. No growth at 10% or more. | 1% yeast extract, 2% soluble starch, 1.5% agar |

*Arai, T. and Y. Mikami: Chromogenicity of Streptomyces. Appl. Microbiol. 23: 402-406, 1972.

TABLE III
Carbohydrate Utilization of Strain C38291

| | |
|---|---|
| Glycerol | + |
| D(−)-Arabinose | ± |
| L(+)-Arabinose | + |
| D-Xylose | ± |
| D-Ribose | + |
| L-Rhamnose | + |
| D-Glucose | + |
| D-Galactose | + |
| D-Fructose | + |
| D-Mannose | + |
| L(−)-Sorbose | − |
| Sucrose | + |
| Lactose | + |
| Cellobiose | + |
| Melibiose | − |
| Trehalose | + |
| Raffinose | − |
| D(+)-Melezitose | − |
| Soluble starch | + |
| Cellulose | − |
| Dulcitol | − |
| Inositol | ± |
| D-Mannitol | + |
| D-Sorbitol | − |
| Salicin | + | observed after incubation at 28° C. for 3 weeks.
Basal medium: Pridham-Gottlieb's inorganic medium
Abbreviation: +: positive utilization, −: negative utilization, ±: doubtful utilization The morphological, cultural and physiological characteristics of strain C38291 described above are consistent with those of the genus Streptomyces. According to the descriptions of Bergey's Manual, strain C38291 should be placed in the following species group: section Spirales or Retinaculum-Apertum, gray series, non-chromogenic and spiny spore surface. This group includes 24 species. Based on the descriptions of ISP species, strain C38291 resembles Streptomyces canus ISP 5017, S. albaduncus strain No. 13246-28-4-27 (J. Antibiotics 17: 39-47 (1964), and S. olivoviridis ATCC 15882 in its spore chain morphology, NaCl tolerance and carbohydrate utilization. Strain C38291 is similar to S. griseoincarnatus ATCC 23917 in the carbohydrate utilization pattern and the formation of reddish diffusible pigment, but differs distinctly from the latter in its grayish aerial mycelium. As a result of direct comparison with the above-mentioned four reference Streptomyces species, strain C38291 is considered to be most similar to strain No. 13246-28-4-27 of Streptomyces albaduncus ATCC 14698, although some differences are noted between the two strains such as the formation of non-diffusible green pigment. Strain C38291, therefore, is considered to be a novel strain of Streptomyces albaduncus.

Since the Streptomyces are easily mutated naturally or artificially, the present invention includes within its scope Streptomyces albaduncus strain C38291 (ATCC 39151) and all natural and artificial albacarcin M- and/or albacarcin V-producing variants and mutants thereof.

Antibiotic Production

The albacarcin V and M antibiotics of the present invention are prepared by cultivating an albacarcin V- and albacarcin M-producing strain of Streptomyces albaduncus, preferably a strain of Streptomyces albaduncus having the identifying characteristics of strain C38291 (ATCC 39151) or a mutant or variant thereof, in a conventional aqueous nutrient medium. The organism is grown in a nutrient medium containing known nutritional sources for actinomycetes, i.e. assimilable sources of carbon and nitrogen plus optional inorganic salts and other known growth factors. Submerged aerobic conditions are preferably employed for the production of large quantities of antibiotic, although for production of limited amounts, surface cultures and bottles may also be used. The general procedures used for the cultivation of other actinomycetes are applicable to the present invention.

The nutrient medium should contain an appropriate assimilable carbon source such as glycerol, L(+)-arabinose, ribose, glucose, fructose, mannose, sucrose, lactose, cellobiose, soluble starch or mannitol. As nitrogen source, ammonium chloride, ammonium sulfate, urea, ammonium nitrate, sodium nitrate, etc. may be used either alone or in combination with organic nitrogen sources such as peptone, meat extract, yeast extract, corn steep liquor, soybean powder, cotton seed flour, etc. There may also be added if necessary nutrient inorganic salts to provide sources of sodium, potassium, calcium, ammonium, phosphate, sulfate, chloride, bromide, carbonate, zinc, magnesium, manganese, cobalt, iron, and the like.

Production of the albacarcin V and M antibiotics can be effected at any temperature conducive to satisfactory growth of the producing organism, e.g. 25°-45° C., and is most conveniently carried out at a temperature of around 27°-32° C. Ordinarily, optimum production is obtained in shaker flasks after incubation periods of 6-8 days. When tank fermentation is to be carried out, it is desirable to produce a vegetative inoculum in a nutrient broth by inoculating the broth culture with a slant or soil culture or a lyophilized culture of the organism. After obtaining an active inoculum in this manner, it is transferred aseptically to the fermentation tank medium. Antibiotic production may be monitored by high performance liquid chromatography assay or by a conventional biological assay.

Isolation and Purification

A preferred isolation and purification scheme for albacarcins V and M is shown below.

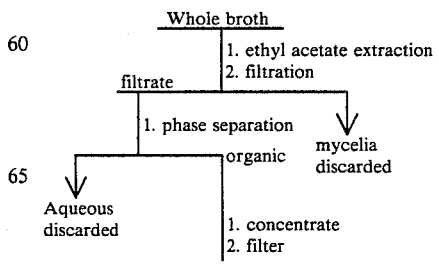

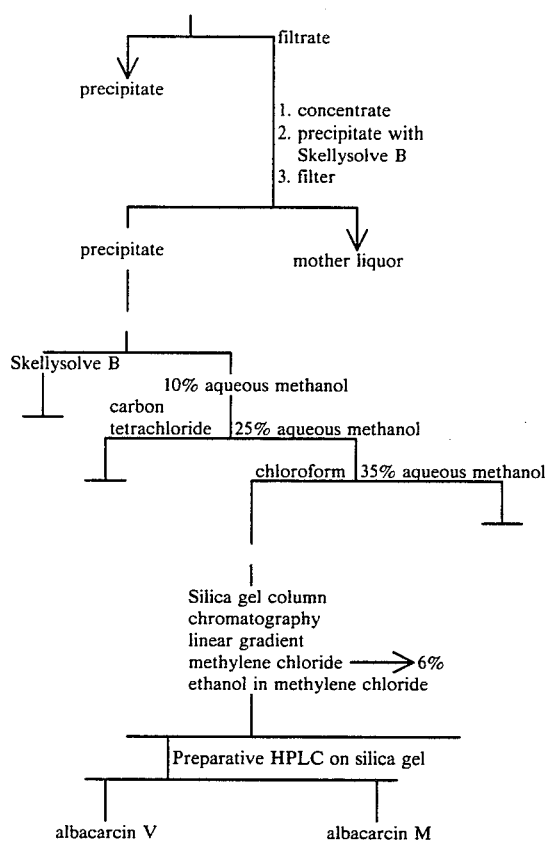

To elaborate on the isolation and purification procedure, albacarcins V and M exist mainly mycelial bound, although a small portion of the antibiotic activity is in the liquid part of the fermented broth. The whole fermentation broth is first extracted with a suitable water-immiscible organic solvent such as ethyl acetate. Filter aid may be optionally employed at this stage to facilitate filtration. The organic solvent extract is then filtered. Filtrate is then concentrated and filtered. The mycelial mat from the harvested broth is extracted with the organic extraction solvent, e.g. ethyl acetate, and the organic solvent extract filtered. Filtrate from the mycelial extraction step is combined with filtrate from the broth extraction. The combined filtrates are then concentrated and the active solids precipitated with a suitable antisolvent such as heptane or Skellysolve B. The precipitated solids are collected by filtration and subjected to a liquid partition procedure.

For the liquid partition, the crude precipitated solids are suspended in a mixture of methanol and Skellysolve B. The resultant suspension is transferred to a separatory funnel and diluted with water. Upon shaking and separation of the phases, the aqueous methanol phase is transferred to a second separatory funnel, diluted with water and extracted with carbon tetrachloride which has been previously saturated with 25% aqueous methanol. The aqueous methanol phase is separated, diluted with water and extracted with chloroform which has previously been saturated with 35% aqueous methanol. All of the suspended solids dissolve at this point. The chloroform extract is then concentrated to dryness to provide a crude complex of albacarcins V and M.

The crude antibiotic complex is then subjected to silica gel column chromatography. Elution is carried out with a linear gradient of methylene chloride to 6% absolute ethanol in methylene chloride. Active fractions are pooled and concentrated in vacuo to provide a mixture of albacarcin V and M.

Final separation and purification of the albacarcin V and M components may be achieved by preparative high performance liquid chromatography as described below in Example 2.

Biological Properties of Albacarcin V and M

The antibacterial activities of albacarcin V and M were determined by a serial two-fold agar dilution method. The results shown in Table IV below indicate that both albacarcin V and M possess moderate gram-positive antibacterial activity with albacarcin V being more potent than albacarcin M. Little or no gram-negative activity was observed at the highest dose tested.

TABLE IV

| | | Minimum Inhibitory Concentration (mcg/ml) | |
|---|---|---|---|
| | | Albacarcin | |
| Organism | Strain No. | M | V |
| Streptococcus pneumoniae | 9585 | 0.4 | 0.025 |
| Streptococcus pyogenes | 9604 | 1.6 | 0.05 |
| Staphylococcus aureus | 9497 | 0.8 | 0.0125 |
| Staphylococcus aureus | 9537 | 3.2 | 0.0125 |
| Staphylococcus aureus | 9606 | 3.2 | 0.4 |
| Staphylococcus aureus | 20688 | 1.6 | 0.1 |
| Escherichia coli | 15119 | >50 | >50 |
| Escherichia coli | 20341-1 | >50 | >50 |
| Klebsiella pneumoniae | 15130 | >50 | >50 |
| Proteus mirabilis | 9900 | >50 | >50 |
| Proteus vulgaris | 21559 | >50 | 3.2 |
| Serratia marcescens | 20019 | >50 | >50 |
| Enterobacter cloacae | 9659 | >50 | >50 |
| Pseudomonas aeruginosa | 9843A | >50 | >50 |

The antitumor activities of albacarcins V and M were demonstrated by a test against P388 leukemia in mice, the results of which are shown in the following Table. Details of the methods used in this procedure have been described in *Cancer Chemother. Rep.* 3: 1–87 (Part 3), 1972.

Albacarcins V and M were found to significantly prolong host survival in the P388 leukemia screening test. Based on comparing both the optimum doses (maximum T/C value) and minimum effective doses (lowest dose giving a T/C>125), albacarcin V appears to be twice as potent as albacarcin M.

TABLE V

| Effect of Albacarcin M and V on P-388 Leukemia | | | | |
|---|---|---|---|---|
| Material | Dose mg/kg/inj | MST Days | Effect MST % T/C | Survivors Day 5 |
| Albacarcin M | 256 | 16.0 | 200 | 6/6 |
| | 128 | 14.0 | 175 | 6/6 |
| | 64 | 12.0 | 150 | 6/6 |
| | 32 | 12.0 | 150 | 6/6 |
| | 16 | 9.5 | 119 | 6/6 |
| | 8 | 9.0 | 113 | 6/6 |
| Albacarcin V | 256 | 8.0 | 100 | 5/6 |
| | 128 | 16.0 | 200 | 6/6 |
| | 64 | 15.5 | 194 | 6/6 |
| | 32 | 12.0 | 150 | 6/6 |
| | 16 | 10.5 | 131 | 6/6 |
| | 8 | 9.0 | 113 | 6/6 |

Host: CDF$_1$ ♀ mice
Treatment: 3X, Days 1,4,7
Evaluation: MST = median survival time
Effect: % T/C = (MST treated/MST control) × 100
Criteria: % T/C ≧ 125 considered significant antitumor activity.

As shown above, albacarcins V and M possess antibacterial activity against gram-positive bacteria and are thus useful in the therapeutic treatment of mammals and other animals for infectious diseases caused by such bacteria. Additionally, the antibiotics may be used for other conventional applications of antibacterial agent such as disinfecting medical and dental equipment.

The marked antitumor activity demonstrated against P388 leukemia in mice indicates that albacarcin V and M are also therapeutically useful in inhibiting the growth of mammalian tumors in experimental animals.

The present invention, therefore, provides a method for therapeutically treating an animal host affected by a bacterial infection or an experimental animal host affected by a malignant tumor which comprises administering to said host an effective antibacterial or tumor-inhibiting amount of albacarcin V or albacarcin M or a mixture thereof or pharmaceutical composition thereof.

In another aspect the present invention provides a pharmaceutical composition which comprises an effective antibacterial or tumor-inhibiting amount of albacarcin V or M in combination with an inert pharmaceutically acceptable carrier or diluent. Such composition may be made up in any pharmaceutical form appropriate for parenteral administration.

Preparations according to the invention for parenteral administration include sterile aqueous or non-aqueous solutions, suspensions or emulsions. They may also be manufactured in the form of sterile solid compositions which can be dissolved in sterile water, physiological saline or some other sterile injectable medium immediately before use.

It will be appreciated that the actual preferred amounts of the albacarcin V or M antibiotic used will vary according to the particular composition formulated, the mode of application and the particular situs, host and disease being treated. Many factors that modify the action of the drug will be taken into account by those skilled in the art, for example, age, body weight, sex, diet, time of administration, route of administration, rate of excretion, condition of the host, drug combinations, reaction sensitivities and severity of the disease. Administration can be carried out continuously or periodically within the maximum tolerated dose. Optimal application rates for a given set of conditions can be ascertained by those skilled in the art using conventional dosage determination tests in view of the above guidelines.

The following examples are provided for illustrative purposes only and are not intended to limit the scope of the invention. Skellysolve B is a commercially available petroleum solvent (Skelly Oil Co.) comprising isomeric hexanes and having a boiling point of 60°–68° C.

EXAMPLE 1

Fermentation of albacarcins V and M

A. Shake-flask Fermentation

*Streptomyces albaduncus* strain C38291 was maintained and transferred in test tubes on agar slants of yeast-malt extract agar. This medium consists of 4 g glucose, 4.0 g yeast extract, 10 g malt extract and 20 g agar made up to one liter with distilled water. With each transfer, the agar slant culture was incubated for seven days at 27° C. To prepare an inoculum for the production phase the surface growth from the slant culture was transferred to a 500 ml Erlenmeyer flask containing 100 ml of sterile medium consisting of 30 g glucose, 10 g soy flour, 10 g cottonseed embryo meal and 3 g $CaCO_3$ made up to one liter with distilled water. This vegetative culture was incubated at 27° C. for 48 hours on a Gyrotory tier shaker (Model G53, New Brunswick Scientific Co., Inc.) set at 230 rev/min describing a circle with a 5.1 cm diameter. Four ml of vegetative culture was transferred to a 500 ml Erlenmeyer flask containing 100 ml of sterile production medium consisting of 60 g glucose, 10 g soy flour, 10 g linseed meal, 0.5 g $FeSO_4.7H_2O$, 1.0 g $NH_4H_2PO_4$ and 10 g $CaCO_3$ made up to one liter with distilled water. The production culture was incubated at 27° C. on a shaker such as used for the vegetative culture which was agitated at 230 rev/min. At 196 hours albacarcin V yield was 1340 $\mu g/ml$ and albacarcin M yield was 500 $\mu g/ml$.

B. Tank Fermentation

For production of albacarcin V and M in a tank fermentor, 1.9 liters of vegetative culture was transferred to a stainless steel tank fermentor containing 30 liters of production medium previously described. The temperature was maintained at 27° C. The air-flow rate was 70 liters/min, the back pressure was 1 atm. and the agitation rate was 375 rev/min. Polypropylene glycol was used to control foaming. After 134 hours the albacarcin V level was 740 $\mu g/ml$ and albacarcin M level was 500 $\mu g/ml$.

C. Large Scale Tank Fermentation

For large scale production of albacarcin V and M in a tank fermentor, 1 liter of vegetative culture (prepared according to the general procedure of Example 1A) was transferred to a tank fermentor containing sufficient seed medium so as to bring the total volume to 375 liters. Seed medium consisted of cerelose (3%), soy flour (1.0%), Pharmamedia (1.0%), $CaCO_3$ (0.3%) and polypropylene glycol (0.05%) in tap water. The seed culture was incubated at 27° C. The air-flow rate was 100 liters/minute, the back pressure was 5 pounds/sq in and the agitation rate was 155 rev/min. After incubation at 48 hours, 150 liters of the seed culture was transferred to a 4500 liter tank fermentor containing sufficient production medium so as to bring the total volume to 3000 liters. Production medium consisted of cerelose (6.0%), soy flour (1.0%), linseed meal (1.0%), $FeSO_4.7H_2O$ (0.05%), $(NH_4)H_2PO_4$ (0.1%) and $CaCO_3$ (1.0%) in tap water. Incubation was carried out at 27° C. with an air-flow rate of 1400 liters/minute, a back pressure of 15 pounds/sq in and an agitation rate of 155 rev/min. After an incubation period of 156 hours, the albacarcin V level was 650 $\mu g/ml$ and the albacarcin M level was 430 $\mu g/ml$.

EXAMPLE 2

Isolation of Albacarcins V and M

Step A. Extraction

Raw fermentation whole broth (~8 l) was transferred to a 80 l polyethylene tank (48 cm diameter top, 44 cm diameter bottom, 55 cm high) equipped with a faucet at the bottom. An equal volume of ethyl acetate was added. The mixture was stirred with an air driven stirrer at a good mixing speed for 30 min. Approximately 6 l (2 kg) of Dicalite was added and mixed. The mixture was filtered on a Dicalite pad which was held in a No. 12 Buchner funnel. The filtrate was collected in a 19 l solution bottle equipped with a vacuum take off. The mat was washed with 2 l of ethyl acetate. The filtrate was transferred to a 20 l separatory funnel and the phases allowed to separate. Occasionally, an emulsion was encountered, and this was separated by passing it through a DeLaval Gyro-tester centrifuge and collecting the resultant phases. The ethyl acetate extract was concentrated to approximately 1 l in a laboratory size glass circulating evaporator equipped with a continuous feed. Any precipitate which formed was collected by filtration. The filtrate was concentrated further to approximately 50 ml in vacuo in a rotatory evaporation. A precipitate was formed by diluting the concentrate with 1500 ml of Skellysolve B. The precipitate was collected by filtration to yield approximately 8.3 g of crude solid.

Step B. Liquid Partition of Crude Solid

The crude solid from Step A (8 g) was suspended in 400 ml of methanol and 400 ml of Skellysolve B using an ultrasonic cleaner. The fine suspension was transferred to a 1 l separatory funnel and diluted with 44 ml of water. The mixture was shaken and the resultant phases allowed to separate. The aqueous methanol (lower phase) and suspended solids were transferred to a second separatory funnel. The aqueous methanol phase was extracted three more times with 300 ml aliquots of Skellysolve B. The Skellysolve B had previously been saturated with an equal volume of 10% water in methanol. The aqueous methanol phase was diluted with 89 ml of water and extracted four times with 300 ml portions of carbon tetrachloride. The carbon tetrachloride was previously saturated with an equal volume of 25% water in methanol. The aqueous methanol phase was diluted with 82 ml of water and extracted four times with 300 ml portions of chloroform. The chloroform was previously saturated with an equal volume of 35% water in methanol. All of the suspended solids dissolved at this point. The chloroform extracts were pooled and evaporated to dryness in vacuo in a rotatory evaporator to yield 6.2 g of crude albacarcin complex.

Step C. Column Chromatography of Crude Complex

A 2.0 cm ID×60 cm Glenco Series 3500 Universal LC column was packed with 63 g of Woelm silica gel (70–230 mesh) in methylene chloride. Crude albacarcin complex (1.1 g) was dissolved in 100 ml of chloroform (2 parts) in methanol (1 part). Approximately 7 g of Woelm silica gel was added to this solution. The solvent was removed from the mixture in vacuo in a rotatory evaporator. The resultant powder was slurried in methylene chloride and added to the above column. Using a Glenco gradient elution apparatus consisting of two chambers of equal diameter, height and volume connected in tandem with Teflon valves, elution commenced with a 4 l linear gradient of methylene chloride to 6% absolute ethanol in methylene chloride collecting 20–200 ml fractions. Aliquots (25 μl) of each fraction were spotted on a Whatman LK5DF silica gel tlc plate. The plate was developed with a 6% absolute ethanol in methylene chloride. The desired compounds were detected in fractions 9–17 after viewing the plate with 366 nm ultraviolet light. These were pooled and evaporated in vacuo in a rotatory evaporator to yield 889 mg of albacarcin V and M mixture. The chromatography was repeated with fresh crude complex as often as needed to provide albacarcin mixture for subsequent purifications.

Step D. Preparative HPLC of Albacarcin V/M Mixture

Preparative HPLC was carried out with a Waters Associates Prep LC/System 500 instrument charged with two silica gel cartridges (Waters PrepPak-500/Silica). The dry columns were wetted and purged of air with methylene chloride (approximately 1 liter). The wet columns were equilibrated with 4 l of 3.5% absolute ethanol in methylene chloride prior to injection of sample. A flow rate of 350 ml/min was used during initial runs. As the columns aged, the flow rate was decreased in 50 ml/min increments to 250 ml/min and the chamber pressure gradually increased from 23 atmospheres to 28 atmospheres. The effluent was monitored with an ISCO model UA-5 absorbance detector at 340 nm–0.5 OD.

Albacarcin V and M mixture (1.08 g) was dissolved in 3 ml of dimethylsulfoxide. The solution was diluted with 3 ml of methylene chloride and injected immediately into the Prep LC/System 500 instrument. Elution commenced using the following program:

1. 1 eluant to waste
2. Collect 6–500 ml fractions
3. Recycle for 8 min 32 sec
4. Collect 7–500 ml fractions
5. Recycle for 5 min 43 sec
6. Collect 500 ml fractions The program was adjusted as changes were made in flow rate to achieve the same elution profile and fraction distribution as above. Fractions 5 and 6 of the first set, fractions 6 and 7 of the second set, and fractions 6 through 11 of the third set of fractions were pooled and evaporated to approximately 50 ml. A precipitate was created by adding 1500 ml of Skellysolve B. The precipitate was collected by filtration to yield 0.54 g albacarcin V. Fractions 1 through 4 of the first set and fractions 14 through 17 of the third set of fractions were pooled and evaporated to about 50 ml. Approximately 1500 ml of Skellysolve B was added and a light yellow precipitate resulted. The precipitate was collected by filtration to yield approximately 300 mg of albacarcin M. The resultant products were assayed by analytical HPLC.

Analytical HPLC of Albacarcins V and M

The following components were used to construct an analytical HPLC system: Waters Associates Model 6000A Solvent Delivery System pump; Varian Varichrom Model VUV-10 uv/vis detector set at 390 nm 0.1 O.D.; Fisher Recorder Series 5000 recorder; Alltech μBondapak $C_{18}$ (10μ) column (4.6 mm ID×25 cm) with a Whatman CoPell ODS (0.03–0.38 mm) guard column (4.6 mm ID×5 cm). The components were connected with 316 stainless steel tubing (1.6 mm OD–0.12 mm ID). Eluant was pumped at a rate of 2 ml/min.

Using 3 parts water in 2 parts tetrahydrofuran, albacarcin M ($k'=1.12$) and albacarcin V ($k'=1.61$), as isolated above, were judged to be 88% and 95.5% pure, respectively.

Step E. Final Purification

After numerous preparative runs of additional lots of albacarcin M and V mixture, the nearly pure albacarcins were rechromatographed by preparative HPLC, as described above, to yield pure albacarcin M and V which have the physical and spectral properties disclosed earlier in the present specification.

We claim:

1. The antibiotic albacarcin M having the formula

15
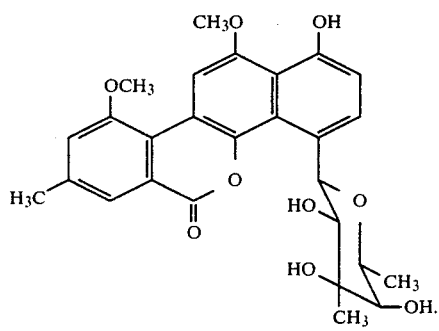
2. The antibiotic albacarcin V having the formula
16
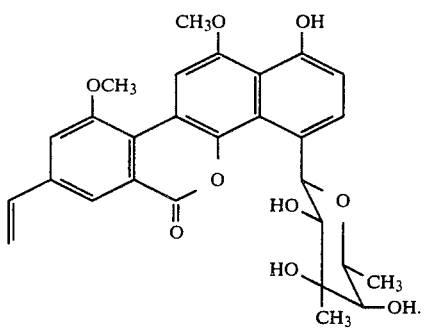
* * * * *